US009782305B2

(12) United States Patent
Mukai et al.

(10) Patent No.: US 9,782,305 B2
(45) Date of Patent: Oct. 10, 2017

(54) ABSORBENT ARTICLE AND METHOD OF MANUFACTURING ABSORBENT ARTICLE

(71) Applicant: UNICHARM CORPORATION, Shikokuchuo-shi, Ehime (JP)

(72) Inventors: Hirotomo Mukai, Kanonji (JP); Kenji Takeuchi, Kanonji (JP); Takaya Arayama, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 402 days.

(21) Appl. No.: 14/408,107

(22) PCT Filed: Jun. 18, 2013

(86) PCT No.: PCT/JP2013/066759
§ 371 (c)(1),
(2) Date: Dec. 15, 2014

(87) PCT Pub. No.: WO2013/191185
PCT Pub. Date: Dec. 27, 2013

(65) Prior Publication Data
US 2015/0173972 A1    Jun. 25, 2015

(30) Foreign Application Priority Data
Jun. 18, 2012    (JP) ................................ 2012-137206

(51) Int. Cl.
*A61F 13/15*    (2006.01)
*A61F 13/20*    (2006.01)
(Continued)

(52) U.S. Cl.
CPC .. *A61F 13/49019* (2013.01); *A61F 13/15593* (2013.01); *A61F 13/15699* (2013.01);
(Continued)

(58) Field of Classification Search
CPC .......... A61F 13/15593; A61F 13/49011; A61F 13/49017; A61F 13/49019; A61F 13/496
See application file for complete search history.

(56) References Cited

U.S. PATENT DOCUMENTS

| | | | |
|---|---|---|---|
| 4,081,301 A | 3/1978 | Buell | |
| 2002/0007172 A1* | 1/2002 | Takei | A61F 13/15601 604/385.27 |

(Continued)

FOREIGN PATENT DOCUMENTS

| | | |
|---|---|---|
| EP | 0761194 A2 | 3/1997 |
| EP | 1384459 A2 | 1/2004 |

(Continued)

OTHER PUBLICATIONS

Office Action dated Nov. 4, 2015, corresponding to Chinese Patent Application No. 201380032087.4.

(Continued)

*Primary Examiner* — Michele M Kidwell
(74) *Attorney, Agent, or Firm* — Hauptman Ham, LLP

(57) ABSTRACT

An absorbent article is provided with a central elastic material for positioning in a state in which it is extended in the front/rear direction in the outer direction in relation to an absorbent body, and an elastic material cover sheet which abuts the outer direction side surface of the central elastic material. The elastic material cover sheet covers an extension region where the central elastic material is positioned in an extended state, and a non-extension region where the central elastic material is positioned in a non-extended state. An adhesive agent for fixing in the extended state is coated onto the central elastic material of the extension region. An adhesive agent is coated onto at least the non-extension region of the outer direction side surface of the elastic material cover sheet, and the adhesive agent coated onto the outer direction side surface penetrates to the inner direction side surface of the elastic material cover sheet.

6 Claims, 10 Drawing Sheets

(51) Int. Cl.
*A61F 13/49* (2006.01)
*A61F 13/53* (2006.01)
*A61F 13/514* (2006.01)
*A61F 13/535* (2006.01)
*A61F 13/496* (2006.01)

(52) U.S. Cl.
CPC ...... *A61F 13/15707* (2013.01); *A61F 13/496* (2013.01); *A61F 13/49011* (2013.01); *A61F 13/49017* (2013.01); *A61F 13/51464* (2013.01); *A61F 13/53* (2013.01); *A61F 13/535* (2013.01)

(56) References Cited

U.S. PATENT DOCUMENTS

| | | | |
|---|---|---|---|
| 2005/0096624 | A1 | 5/2005 | Hoshino et al. |
| 2009/0124992 | A1 | 5/2009 | Wright et al. |
| 2010/0262101 | A1* | 10/2010 | Minato .............. A61F 13/4942 604/365 |
| 2013/0110075 | A1 | 5/2013 | Mukai et al. |

FOREIGN PATENT DOCUMENTS

| | | |
|---|---|---|
| EP | 1723939 A1 | 11/2006 |
| EP | 2412352 A1 | 2/2012 |
| JP | 2006-346439 A | 12/2006 |
| JP | 3873894 B2 | 1/2007 |
| WO | 2004/087416 A1 | 10/2004 |
| WO | 2011132688 A1 | 10/2011 |

OTHER PUBLICATIONS

Office Action in JP Application No. 2012-137206, mailed Dec. 22, 2015.

Extended European Search Report in EP Application No. 13807667.4 dated Jan. 22, 2016.

International Search Report mailed Sep. 24, 2013 in International Application No. PCT/JP2013/066759 filed Jun. 18, 2013.

* cited by examiner

ABSORBENT ARTICLE AND METHOD OF MANUFACTURING ABSORBENT ARTICLE

RELATED APPLICATIONS

The present application is a National Phase of International Application Number PCT/JP2013/066759 filed Jun. 18, 2013, which claims priority to Japanese Application Number 2012-137206 filed Jun. 18, 2012.

TECHNICAL FIELD

The present invention relates to an absorbent article and a method of manufacturing the absorbent article having an elastic member which is stretched in a longitudinal direction or in a widthwise direction of the absorbent article.

BACKGROUND ART

Patent Literature 1 discloses a method of manufacturing an absorbent article which alternately forms: a stretch region in which an elastic member in a stretched state is arranged between two sheets which constitute a disposable diaper as an absorbent article; and a non-stretch region in which an elastic member in a non-stretched state is disposed.

In the method of manufacturing the absorbent article set forth in Patent Literature 1, an adhesive agent is applied to at least one of two sheets so as to form a strong adhesive unit and a weak adhesive unit, and then, an elastic member is disposed in a stretched state and is secured at the strong adhesive unit, and thereafter, the elastic member is cut at the weak adhesive unit. The elastic member that has been in the stretched state at the weak adhesive unit shrinks, and only the elastic member that has been secured by a strong adhesive agent still remains In this manner, a stretch region and a non-stretch region are formed.

As a method of forming a strong adhesive unit and a weak adhesive unit at two sheets, there are exemplified: a method of applying an adhesive agent to one of the sheets while varying the amount of application; a method of alternately disposing two kinds of adhesive agents with their adhesive forces which are different from each other; and a method of intermittently applying an adhesive agent to a sheet.

CITATION LIST

Patent Literature

[Patent Literature 1]
Japanese Patent No. 3873894

SUMMARY OF INVENTION

Technical Problem

However, in the method of manufacturing the absorbent article, as described above, there has been the following problem that still remains unsolved. If an attempt is made to apply an adhesive agent to a sheet while varying an application amount thereof, an applying device must be controlled so as to adjust the discharge amount of the adhesive agent all the time, and also, it is difficult to adjust the amount of application at a boundary between a strong adhesive unit and a weak adhesive unit, and it is difficult to form the strong adhesive unit and the weak adhesive unit clearly distinctively. Also, if an attempt is made to apply different kinds of adhesive agents, there is a need to respectively control applying devices which correspond to two kinds of adhesive agents, and in addition, it is difficult to adjust the amount of application at the boundary between the strong adhesive unit and the weak adhesive unit, and further, it is difficult to form the strong adhesive unit and the weak adhesive agent clearly distinctively.

In addition, if an attempt is made to discontinuously apply an adhesive agent to a sheet, the adhesive agent is not applied to the weak adhesive unit. If the adhesive agent is not applied to the weak adhesive unit, when an elastic member disposed at the weak adhesive unit is cut, the elastic member disposed at the weak adhesive unit cannot be retained at an intended position, the elastic member having shrunk moves outside of the weak adhesive unit, or alternatively, the elastic member shrinks too much in the weak adhesive unit, and there is an apprehension that a feeling of discomfort in appearance or an impairment of a feeling of comfort at the time of wearing occurs.

Accordingly, it is an object of the present invention to provide an absorbent article and a method of manufacturing the absorbent article that is capable of alternatively disposing an elastic member in a stretched state and an elastic member in a non-stretched state, and that is capable of restraining a feeling of discomfort in appearance or an impairment of a feeling of comfort at the time of wearing while retaining a position or a shape of the elastic member in the non-stretched state An absorbent article (disposable diaper 1) according to the present invention comprises: a longitudinal direction (longitudinal direction L) which extends between a body foreside and a body rearside of a wearer; a widthwise direction (widthwise direction W) perpendicular to the longitudinal direction;

an inner direction (inner direction IN) which is oriented to the wearer;

an outer direction (outer direction OUT) which is oriented to an opposite to the inner direction; a crotch region (crotch region S3) which is applied for a crotch of the wearer; a front waistline region (Front waistline region S1) which is disposed at a front side of the crotch region; a rear waistline region (rear waistline region S2) which is disposed at a rear side of the crotch region;

an absorber which is disposed at least in the crotch region;

an elastic member (central elastic member 44) which is disposed in an extended state in the longitudinal direction in the outer direction than the absorber; and a sheet member (elastic member covering sheet 43) which is disposed on a face of the outer direction of the elastic member, and which abuts against the elastic member, wherein the sheet member is disposed so as to cover: a stretch region (first application region R1) in which the elastic member is disposed in a stretched state in the longitudinal direction; and a non-stretch region (central elastic member non-stretched region R8) in which the elastic member is disposed in a non-stretched state, wherein an adhesive agent is applied to an inner surface or an outer surface of the elastic member in the stretch region, wherein the elastic member in the stretched region is secured to the sheet member by the adhesive agent that is applied to the elastic member in the stretched region, wherein an adhesive agent is applied to an outer surface of the sheet member at least in the non-stretch region, and wherein an adhesive agent permeated by the adhesive agent that is applied to an outer surface of the sheet member is disposed on an inner surface of the sheet member by basis weight which is smaller than that of the adhesive agent that is applied to the elastic member in the stretched region.

A method of manufacturing an absorbent article according to the present invention comprises an absorber having: a longitudinal direction which extends between a body foreside and a body backside of a wearer; a widthwise direction perpendicular to the longitudinal direction; an inner direction which is oriented to the wearer; and an outer direction which is oriented to an opposite to the inner direction, an elastic member which is disposed in an extended state in the longitudinal direction in the outer direction than the absorber; and a first sheet member (elastic member covering sheet 43) and second sheet member (absorber backsheet 30) which is disposed sandwich the elastic member in the outer direction than the absorber. The method comprising: a first step of applying an adhesive agent to the elastic member while conveying the elastic member in a stretched state and then alternately forming, in a direction of the conveyance, an application region in which an adhesive agent is applied to the elastic member and a non-application region in which an adhesive agent is not applied to the elastic member, a second step of applying an adhesive agent to a face which is opposite to the elastic member of the first sheet member so that the adhesive agent permeates the first sheet member in a thickness direction, the second step applying an adhesive agent to at least a position which overlaps with the non-application region; and a third step of cutting the elastic member in the non-application region and then, in the application region, disposing an elastic member in a stretched state.

DESCRIPTION OF EMBODIMENTS

Figure 1:
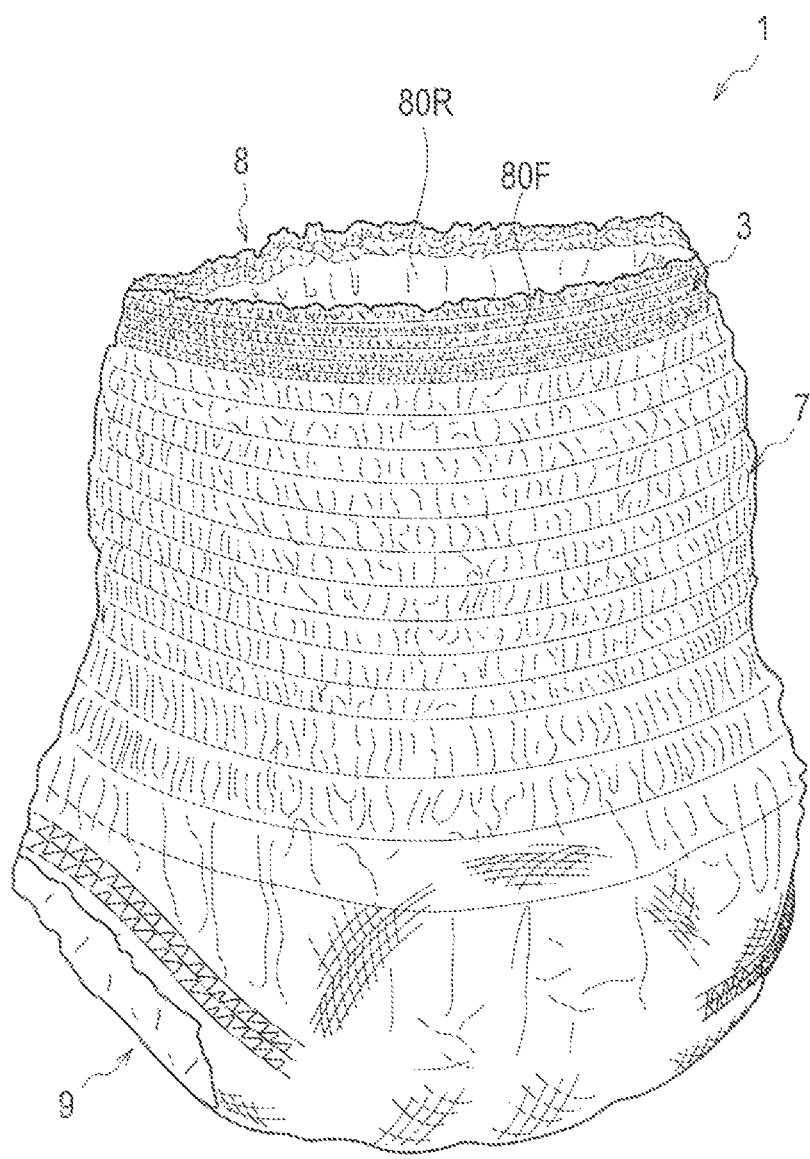
FIG. 1 is a schematic perspective view of a disposable diaper according to a first embodiment.

Hereinafter, a disposable diaper 1 as an absorbent article according to embodiments will be described with reference to the drawings. In the following description of the drawings, the same or similar parts are denoted by the same or similar reference numerals. It should be noted that the drawings are schematic, and the ratios of dimensions and the like are different from the actual ones. Therefore, specific dimensions and the like should be determined by referring to the following description. Of course, the drawings include the parts having different dimensions and ratios.

(1) Overall Schematic Structure of Disposable Diaper

Figure 2:
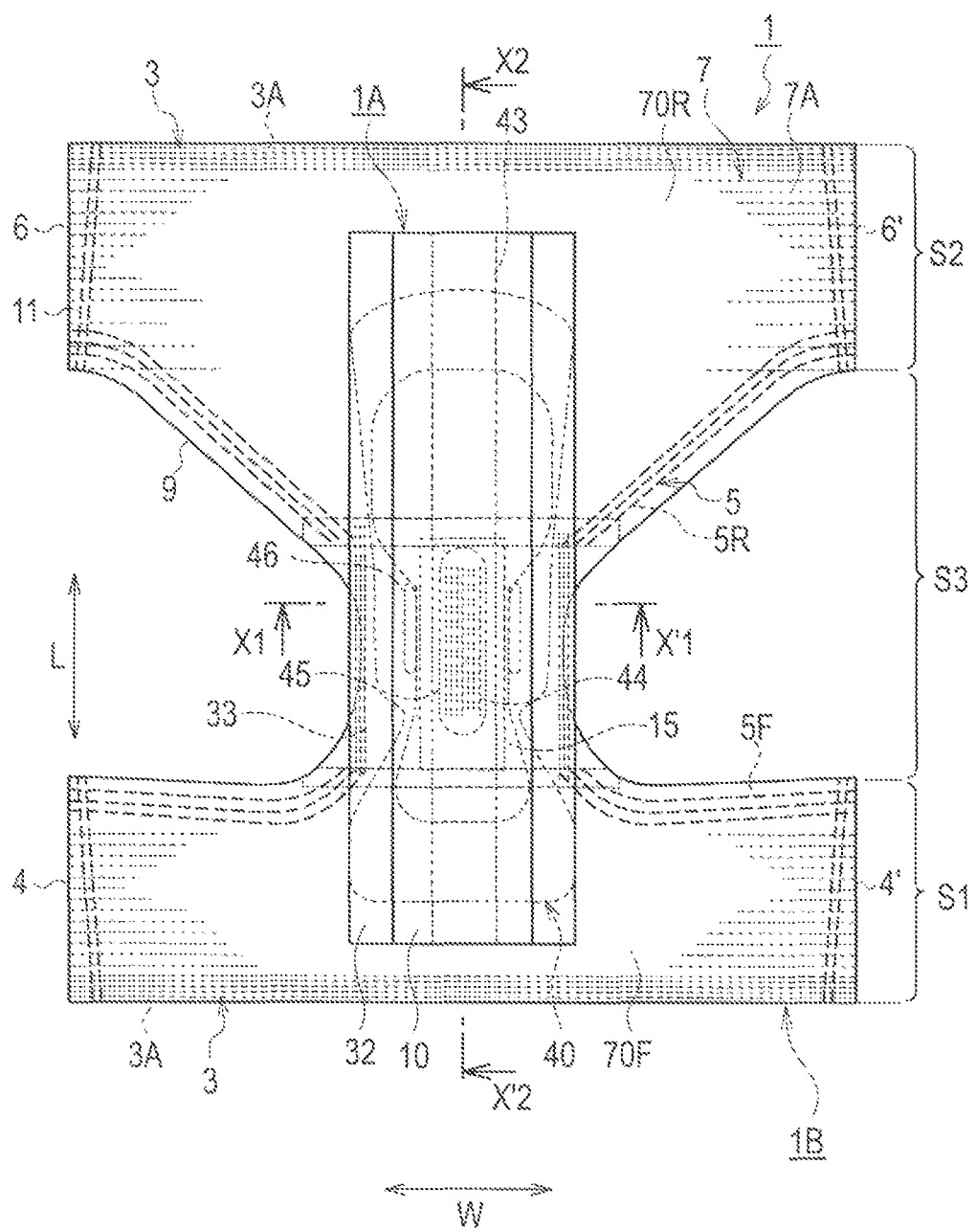
FIG. 2 is an exploded plan view of the disposable diaper according to the first embodiment.
Figure 3:
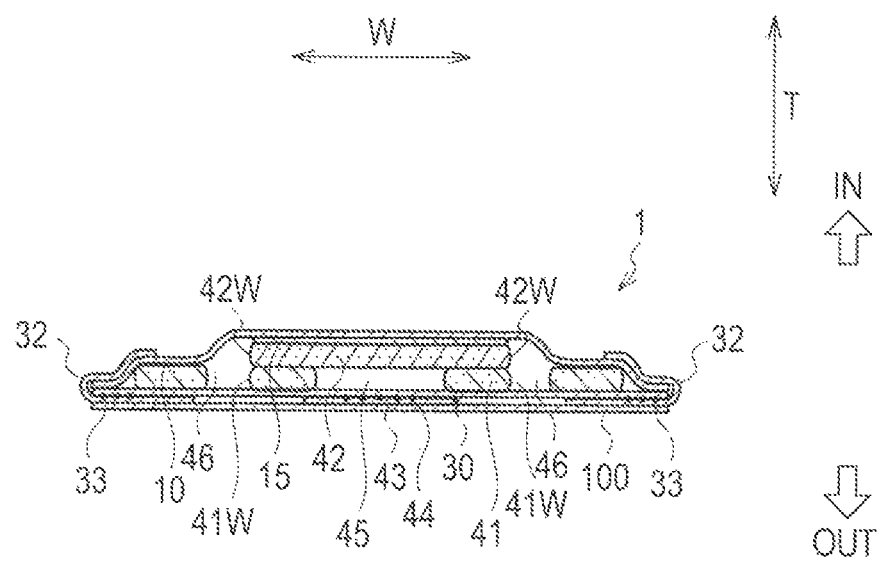
FIG. 3 is a sectional view in a widthwise direction of the disposable diaper taken along the line X1-X'1 shown in FIG. 2.
Figure 4:
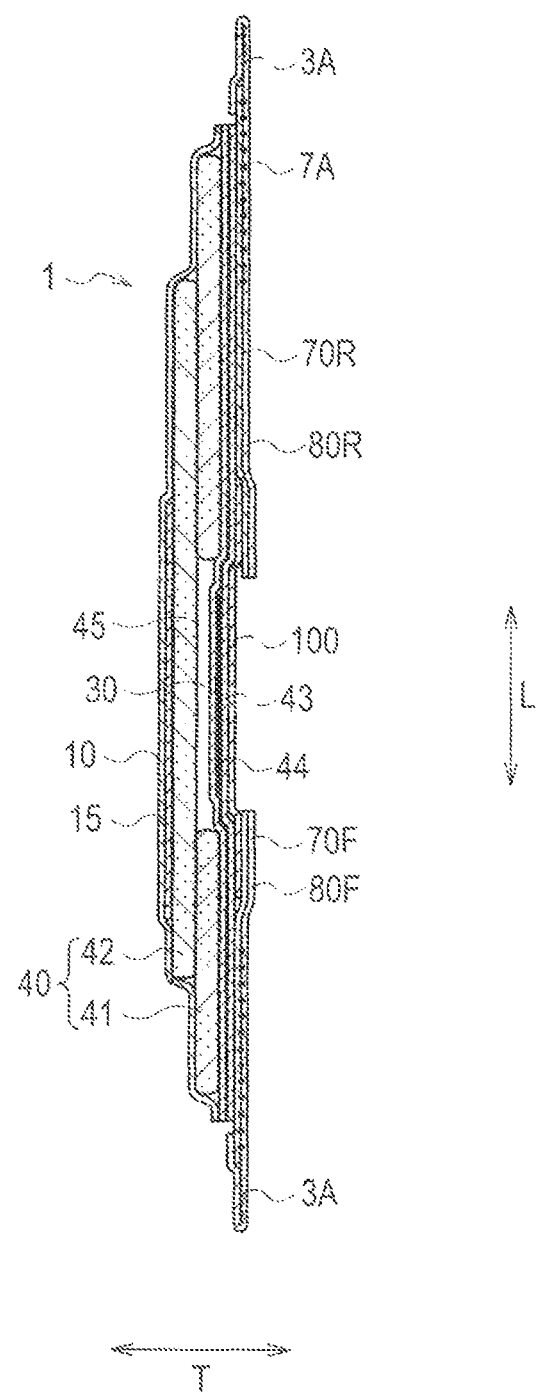
FIG. 4 is a sectional view in a longitudinal direction of the disposable diaper taken along the line X2-X'2 shown in FIG. 2.

FIG. 1 is a schematic perspective view of a disposable diaper which constitutes a disposable diaper 1 in the embodiment. FIG. 2 is an exploded plan view of the disposable diaper 1 according to the embodiment. FIG. 3 is a sectional view in a widthwise direction of the disposable diaper 1 taken along the line X1-X'1 shown in FIG. 2. FIG. 4 is a sectional view in a longitudinal direction of the disposable diaper 1 taken along the line X2-X'2 shown in FIG. 2. The disposable diaper 1 is a pants-type disposable diaper. It is to be noted that the exploded plan view shown in FIG. 2 is a view of a state in which an elastic member such as a leg gather is stretched to an extent such that wrinkles of an absorbent main body and an exterior body constituting the disposable diaper are not formed.

A disposable diaper 1 has: a longitudinal direction L expanding to a body foreside and a body backside of a wearer; a widthwise direction W orthogonal to the longitudinal direction L; and a thickness direction T having an inner direction IN oriented to the wearer and an outer direction OUT oriented to an opposite side to the inner direction.

The disposable diaper 1, as shown in FIG. 2, has, in a longitudinal direction of the disposable diaper 1, a front waistline region 51 which corresponds to a front waistline of a wearer, a rear waistline region S2 which corresponds to a rear waistline of the wearer, and a crotch region S3 which corresponds to a crotch of the wearer, and is positioned between the front waistline region 51 and the rear waistline region S2.

A front waistline edge 4 which is positioned on the outside of a widthwise direction W of the front waistline region 51 is joined with a rear waistline edge 6 which is positioned on the outside of a widthwise direction W of the rear waistline region S2, and a front waistline edge 4' is joined with a rear waistline edge 6', whereby the disposable diaper 1 is formed as the one of the pants type. In the front waistline region and the rear waistline region of the disposable diaper of the pants type, a joining unit 11, both edges of which are joined with each other, is formed, and a crotch region S3 is a region which is on the inside of a longitudinal direction more significantly than the joining unit 11.

In the disposable diaper 1, as shown in FIG. 1, there are formed: a waistline opening unit 8 disposed so as to surround the wearer's waistline and a pair of leg hole opening unit 9 disposed so as to surround the wearer's leg in a state in which it is formed in the shape of a pant.

The disposable diaper 1 includes: an absorbent main body 1A including a topsheet 10, an absorber 40, and an absorber backsheet 30 or the like; and an exterior body 1B including a foreside exterior topsheet 70F, a rearside exterior topsheet 70R, and an exterior backsheet 80 or the like, and these constituent elements are joined to each other by an adhesive or thermal fusion bonding or the like.

The exterior body 1B includes: a foreside exterior topsheet 70F, a rearside exterior topsheet 70R, an a foreside exterior backsheet 80F, a rearside exterior backsheet 80R, an exterior center sheet 100 and constitutes an exterior portion of the disposable diaper 1. The exterior body 1B is positioned in an outer direction OUT more significantly than the absorbent main body 1A including the absorber 40, and is disposed on surface of a non-skin contact side of the disposable diaper.

The foreside exterior topsheet 70F is disposed across the front waistline region S1 and the crotch region S3. The rearside exterior topsheet 70R is disposed across the rear waistline region S2 and the crotch region S3. The foreside exterior topsheet 70F and the rearside exterior topsheet 70R are disposed so as to be spaced from each other in the longitudinal direction, and in the thickness direction, these topsheets are disposed between the front exterior backsheet 80F or the rearside exterior backsheet 80R and the absorbent main body 1A.

The foreside exterior topsheet 70F and the rearside exterior topsheet 70R can be formed by an air-through nonwoven cloth, a spun bond nonwoven cloth, an SMS nonwoven cloth, or a water-resistive film. The foreside exterior topsheet 70F and the rearside exterior topsheet 70R according to the present embodiment are configured by an SMS nonwoven cloth with a basis weight of 15 g/m2 and made from polypropylene.

The foreside exterior backsheet 80F and the rearside exterior backsheet 80R are positioned on the outside at the time of wearing. Namely, these backsheets are disposed at a side which is spaced from a wearer's skin. The foreside exterior backsheet 80F is disposed across the front waistline region S1 and the crotch region S3. The rearside exterior backsheet 80R is disposed across the rear waistline region S2 and the crotch region S3. The foreside exterior backsheet 80F and the rearside exterior backsheet 80R are disposed so as to be spaced from each other in the longitudinal direction. A front end of the foreside exterior backsheet 80F and a rear end of the rearside exterior backsheet 80R are returned at a skin contact surface side, and are disposed so as to envelope the front end of the foreside exterior topsheet 70F and the rear end of the rearside exterior topsheet 70R.

The exterior backsheet can be formed of an air-through nonwoven cloth, a span bond nonwoven cloth, an SMS nonwoven cloth, or a waterproof film or the like. The exterior backsheet according to the embodiment is made of a span bond nonwoven cloth of 18 g/m2 in total weight made of polypropylene.

An exterior center sheet 100 is positioned between a back end of a respective one of the foreside exterior topsheet 70F and the foreside exterior backsheet 80F and a front end of a respective one of the rearside exterior topsheet 70R and the rearside exterior backsheet 80R in the longitudinal direction, and in the thickness direction, the exterior center sheet is positioned between the foreside exterior topsheet 70F and the absorber back sheet 30 or an elastic member covering sheet 43 and between the rearside exterior topsheet 70R and the absorber back sheet 30 or the elastic member covering sheet 43.

By providing the exterior center sheet 100, the foreside exterior topsheet 70F and the foreside exterior backsheet 80F can be connected to each other, and the rear-side exterior topsheet 70R and the rear-side exterior backsheet 80R can be connected to each other. Therefore, in a mode in which the exterior topsheet and the exterior backsheet are spaced from each other in the longitudinal direction, exposure of the absorbent main body 1A to the outside can be prevented. Further, in the course of manufacturing, in a state in which the foreside exterior sheet and the rear-side exterior sheet that are spaced from each other are connected to each other, a leg opening unit can be formed, and these exterior sheets can be bonded with the absorbent main body 1A.

The exterior center sheet 100 can be formed by an air-through nonwoven cloth, a spun bond nonwoven cloth, a SMS nonwoven cloth, or a water-resistive film The exterior center sheet 100 according to at least one embodiment is constituted of a spun bond nonwoven having a basis weight of 19 g/m2 of polypropylene.

The absorbent main body 1A includes a topsheet 10, an auxiliary sheet 15, an absorber backsheet, and a leakage preventing unit, and is disposed is provided closer to the skin contact surface than the exterior body 1B.

The topsheet 10 is a sheet that forms the skin contact surface that can be in direct contact with the skin of the wearer. The topsheet 10 is provided closer to the skin contact surface than the absorber 40. The topsheet 10 is formed by a liquid-permeable sheet, such as a hydrophilic nonwoven cloth and a hydrophilic woven cloth, an aperture plastic film, or an aperture hydrophobic nonwoven cloth. The topsheet 10 according to at least one embodiment is formed of a hydrophilic spun bond nonwoven cloth having a basis weight of 23 g/m2 of polypropylene.

The auxiliary sheet 15 is joined with the non-skin contact surface side of the topsheet 10. The auxiliary sheet 15 is disposed between the topsheet 10 and the absorber 40. Providing the auxiliary sheet 15 makes it possible to increase the speed at which the bodily fluid is absorbed, and makes it possible to prevent reversal of the bodily fluid after absorption.

The auxiliary sheet 15 is made of, for example, an air-through nonwoven cloth, a porous film, or the like. The auxiliary sheet 15 according to the present embodiment is formed of (hydrophilic) air-through nonwoven cloth having a basis weight of 30 g/m2. The topsheet 10 and the auxiliary sheet 15 according to at least one embodiment are joined by adhesive.

The absorber 40 is joined between a composite sheet on which the topsheet 10 and the auxiliary sheet 15 are joined with each other and the absorber backsheet 30 by a hot melt adhesive. The hot melt adhesive is respectively applied to the composite sheet and the backsheet, and is applied at a respective one of the basis weights of 5 g/m2 and 8 g/m2 by a spiral coating method of example.

The absorber 40 is formed of a mixed powder of ground pulp, highly absorbent polymer, and the like. The absorber 40 is configured using a first absorbent layer 41 disposed closer to the non-skin contact surface with the wearer and a second absorbent layer 42 overlapping with the first absorbent layer 41 and disposed closer to the skin contact surface of the wearer (see FIG. 5).

In the first layer 41, a central slit 45 and side slits 46, which extend the longitudinal direction, are formed. The central slit 45 is formed at a center in the widthwise direction of the first layer 41, and the side slits 46 are formed at both outsides of the widthwise direction more significantly than the central slit 45.

The disposable diaper 1 has a central elastic member 44 that is arranged to overlap the central slit 45. With these elastic materials, slits, and the like formed in the absorber 40, the absorber 40 is configured to bend when the disposable diaper 1 is worn. In the present embodiment, the central elastic member 44 and the central slit 45 constitute a curving unit formed to enable the absorber to bend convexly toward the inner direction. Furthermore, the side slits 46 are formed to enable the absorber to bend convexly toward the outer direction. It is to be noted that a structure of the absorber will be described later in detail.

The absorber backsheet 30 is provided at a non-skin contact surface side of the absorber 40. The absorber backsheet 30 is formed of a sheet such as a liquid-impermeable film (for example, polyethylene). The absorber backsheet 30 is disposed in an outer direction OUT more significantly than the absorber, and is formed of a liquid non-permeable. The absorber backsheet 30 is disposed so as to be extensive to the outside in the longitudinal direction more significantly than the absorber 40.

It is sufficient if the absorber back sheet 30 be disposed so as to cover at least a face at the outer side of an absorber, or alternatively, the absorber back sheet may be disposed so as to cover an end in the widthwise direction of the absorber. On a face of the outer side of the absorber back sheet 30, a central elastic member 44 and the elastic member covering sheet 43 are disposed, each of which functions as a leakage preventing sheet.

The leakage preventing unit has a leakage preventing side sheet 32 and a leakage preventing elastic member 33, and is disposed along the longitudinal direction at a widthwise end of the absorber 40. The leakage preventing side sheet 32 is provided so as to integrally envelope the topsheet 10 and the absorber backsheet 30 at both side ends in the widthwise direction W of the absorber 40. The leakage preventing side sheet 32 is formed of a sheet such as a liquid impermeable nonwoven cloth. One end in the widthwise direction of the leakage preventing side sheet 32 is joined with a non-skin surface of the absorber backsheet 30, and the other end in the widthwise direction of the leakage preventing side sheet 32 is folded back from a lateral of absorber 40 in widthwise direction to the top sheet side, and is joined with a face of the skin contact face side of the topsheet 10.

The leakage preventing side sheet 32 is joined with the topsheet or the like by a hot melt adhesive. In the embodiment, a plurality of hot melt adhesives was applied in basis weight of 0.1 g/m2 by bead coating method. In addition, the leakage preventing side sheet 32 is constituted with a sheet of a hydrophobic nonwoven cloth, and in the embodiment, the leakage preventing side sheet 32 is constituted with an SMS nonwoven cloth having a basis weight of 15 g/m2 of polypropylene.

The leakage preventing elastic member 33 is adhered between the absorber backsheet 30 and the leakage preventing side sheet 32 in an expanded state. The leakage preventing elastic member 33 shrinks both ends in the widthwise direction of the absorber respectively in the longitudinal direction, and functions as a side elastic member. A hot melt adhesive can be exemplified as a means for bonding the leakage preventing elastic member. In the embodiment, Spandex is employed as the leakage preventing elastic member 33, and is directly applied by V slot method. More specifically, three leakage preventing elastic members 33 are each expanded and fixed with a thickness of 780 dtex and an expansion magnification of 2.3 times.

The leakage preventing elastic members 33 are disposed so as to substantially communicate with a leg gather to be described later in a planar view. Thus, the leakage preventing elastic members and the leg gather are disposed, whereby there can be attained advantageous effects that the wearer's leg feed can be tightened so as to be surrounded, a fitting feeling of leg feed is improved, and displacement or leakage of the disposable diaper is prevented.

The waist gathers 3 and waistband gathers 7 are provided in the front waistline region S1 and the rear waistline region S2. The waist gathers 3 and the waistband gathers 7 have elongated waist elastic members 3A and waistband elastic members 7A of synthetic rubber or the like that are laid out to stretch along the widthwise direction W of the absorber 40. The waist elastic members 3A and the waistband elastic members 7A are joined between the foreside exterior topsheet 70F and the foreside exterior backsheet 80F, and also between the rearside exterior topsheet 70R and the rearside exterior backsheet 80R with an adhesive (for example, the hot-melt adhesive) in an extended state in the widthwise direction W of the disposable diaper 1.

The waist gathers 3 and the waistband gathers 7 continue from one front waistband edge 4 up to the other front waistband edge 4' positioned on the outside in the widthwise direction W of the absorbent article 1 in the front waistline region S1, and from one rear waistband edge 6 up to the other front waistband edge 6' positioned on the outside in the widthwise direction W of the absorbent article 1 in the rear waistline region S2.

A leg gather 5 is provided at the periphery of a leg-holes opening unit 9. The leg gathers are formed of a synthetic rubber or other elongated leg hole elastic material laid out so as to stretch. The leg hole elastic material is configured by a front leg hole elastic material 5F arranged in the front waistline region S1, and a rear leg hole elastic material 5R arranged in the rear waistline region S2. The leg gathers 5 are provided so as not to cross the absorber 40.

The leg hole elastic material is joined between the foreside exterior topsheet 70F and the foreside exterior backsheet 80F, and between the rearside exterior topsheet 70R and the rearside exterior backsheet 80R.

Arranging the waist gathers 3, the waistband gathers 7, and the leg gathers 5 makes it possible to hold the disposable worn article at the waistline, and makes it possible to prevent the entire disposable worn article from slipping down.

A waist elastic member according to the present embodiment is extended and fixed in sixes at a thickness of 940 dtex and an extension rate of 3.5 times, in both the front waistline region S1 and the rear waistline region S2. Further, the waistband elastic member is extended and fixed at a thickness of 780 dtex and an extension rate of 3.0 times. Examples of means for fixing the hip elastic material and the waistband elastic member may include the hot-melt adhesive. In the present embodiment, the elastic material is directly coated with the hot-melt adhesive using a V-slot method.

Three of the leg hole elastic members of the embodiment are fixed in an extended state at the thickness of 780 dtex and 1.5 to 3.5 times in extension magnification. The leg hole elastic members are arranged at each portion with a different grade in magnification.

The leg hole elastic members are fixed with the hot melt adhesive that was already coated on the exterior topsheet. The hot melt adhesive is coated by a spiral spray. The coating weight of the leg hole elastic members is 7 g/m2. An adhesive is coated by a slot coater at a location where the vicinity of the exterior topsheet ends (at about 5 mm from the ends) overlaps at least the leg hole elastic member. With this adhesive coating, the leg hole elastic members are prevented from hanging down out from the ends of the exterior surface sheet.

When an adhesive is coated by a non-contact type spiral spray, the adhesive near the ends of the exterior topsheet may protrude, causing manufacturing problems. However, an adhesive may be prevented from protruding by coating using a contact type slot coater. The coating weight of the slot coater is 110 g/m2.

The central elastic member 44 is provided at a position having overlap with the central slit 45 in the thickness direction T. The central elastic member 44 is formed so as to be convex in the inner direction IN, i.e., so as to overlap onto the absorber 40 along the front-back direction, such that the absorber 40 bends convexly toward the wearer. Because the central elastic member 44 is arranged to overlap the central slit 45, the central slit 45 can be flexed upward (at the side of the wearer) more stably. The central elastic member 44 is arranged in an extended state along the front-back direction at the center in the widthwise direction of an absorbent article. The central elastic member 44 is arranged at the crotch region S3.

The central elastic member 44 is provided in a stretched state between the elastic member covering sheet 43 as a first sheet member and the absorber back sheet 30 as a second sheet member. The central elastic member 44 is disposed at an expansion rate of 1.4 times to 3.0 times.

The central elastic member according to the embodiment is a spandex with a thickness of 620 dtex, and seven pieces are secured so as to be stretched at an expansion rate of 2.0 times. Intervals of the central elastic member are 5 mm, and a total adhesive length is 120 mm.

The elastic member covering sheet 43 is composed of a sheet such as a nonwoven cloth, and functions as a sheet member which is disposed in an outer direction of the central elastic member as an elastic member. In the embodiment, a span bond nonwoven cloth (hydrophobic) of 15 g/m2 in basis weight, which is made of polypropylene, was employed.

It is preferable that a fiber diameter of a nonwoven cloth constituting the elastic member covering sheet 43 be about 16-30 μm. A diameter of the fiber constituting the nonwoven cloth of the embodiment is about 22 μm. For example, if the fiber diameter of the nonwoven cloth constituting the elastic member covering sheet 43 is thicker or if the elastic member covering sheet 43 is stretched, a gap between the fibers increases, and an adhesive agent is prone to seep; and however, if the fiber diameter is larger in thickness than 30 μm or the elastic member covering sheet 43 is stretched too much, seeping of the adhesive agent is also excessive in amount, and the elastic member may be adhesively bonded in a non-stretch region. Alternatively, if the fiber diameter of the nonwoven cloth constituting the elastic member covering sheet 43 is smaller in thickness than 16 μm, the gap between the fibers is too small, and it is difficult to attain a permeation effect of the adhesive agent which will be described later.

Also, the elastic member covering sheet 43 is not limited to the span bond nonwoven cloth, and there can be employed: an SMS nonwoven cloth made of a combination of a span bond nonwoven cloth and a melt blown nonwoven cloth; an air-through nonwoven cloth; or a span lace nonwoven cloth or the like. In addition, a melt blown layer constituting the SMS nonwoven cloth is the one of 1 μm in fiber diameter or the like, and is smaller in gap than a nonwoven cloth of the same basis weight in comparison with the span bond nonwoven cloth. It is preferable that the basis weight of the nonwoven cloth constituting the elastic member covering sheet 43 be 10 g/m2 to 20 g/m2.

It is to be noted that a method of disposing the central elastic member and the elastic member covering sheet will be described later in detail.

Examples of the material of the central elastic member 44 include synthetic rubber such as styrene-butadiene, butadiene, isoprene, and neoprene, natural rubber, EVA, elastic polyolefin, spandex, and foamed polyurethane. In addition, as the material of the central elastic member 44, an elastic sheet such as a stretching nonwoven cloth formed by mixing and then stretch-processing urethane, polystyrene or other elastomer fiber with stretching polyolefin, polyester, or other thermoplastic fiber, may be used.

As for each member constituting the aforementioned disposable diaper 1, the material described in Japanese Unexamined Patent Application Publication No. 2006-346439, for example, may be used.

(2) Structure of Absorber

Figure 5:
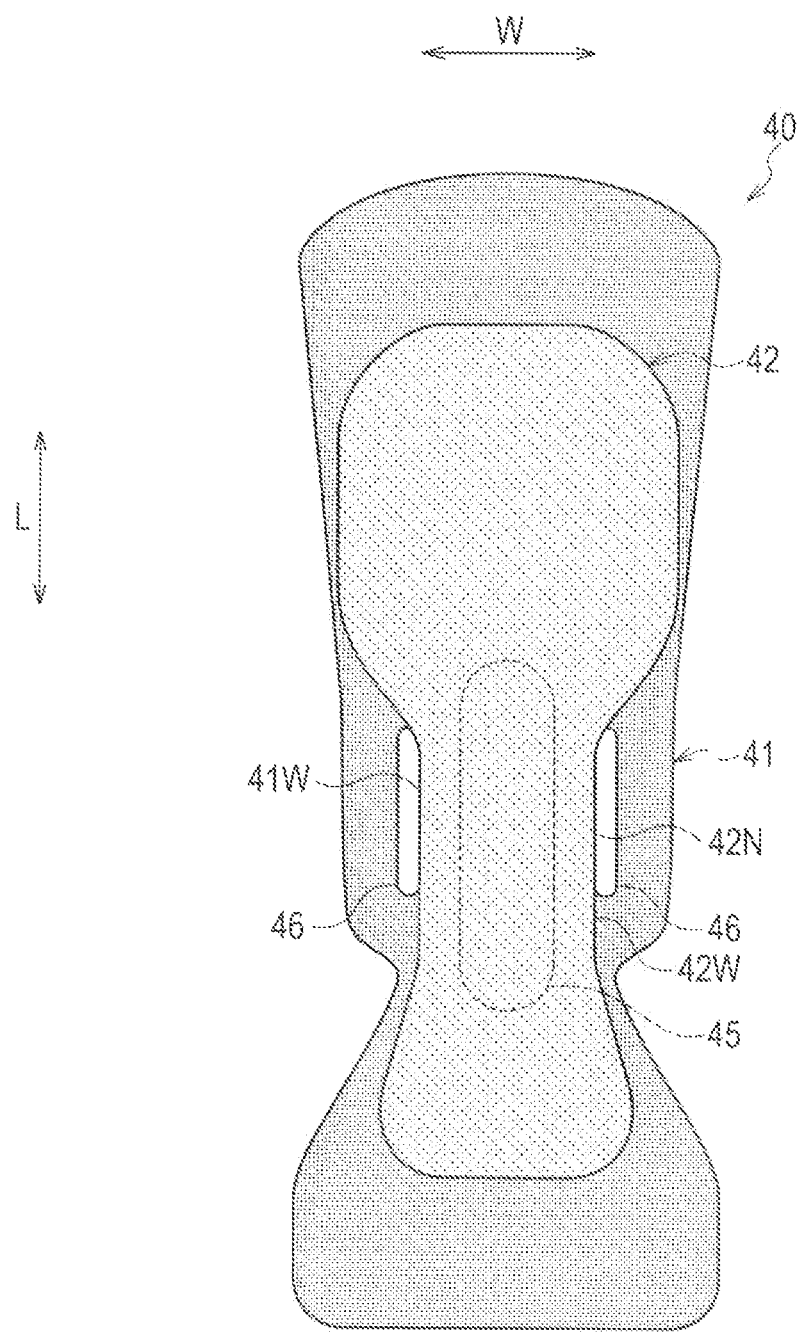
FIG. 5 is a plan view of an absorber according to the first embodiment.

FIG. 5 is a plan view of the absorber 40. As illustrated in FIG. 5, the absorber 40 has a first layer 41, and a second layer 42 on top of the first layer 41. The first layer 41 is positioned at the non-skin contact surface side of the wearer, and the second layer 42 is positioned at the skin contact surface side of the wearer.

A length in the longitudinal direction of the first layer 41 is larger than a length in the longitudinal direction of the second layer 42. The first layer 41 us disposed across the rear waistline region S2, the crotch region S3, and the front waistline region S1, and the second layer 42 is disposed across the crotch region S3 and the front waistline region S1. A length in the widthwise direction of the second layer 42 is smaller than a length in the widthwise direction of the first layer 41. The first layer 41 overhangs to the outside of the widthwise direction more significantly than the second layer 42.

The first layer 41 and the second layer 42 are configured by cotton-like pulp and superabsorbent polymer (SAP).

The first layer 41 is, for example, formed by mixing 100 to 500 g/m2 of pulp and 20 to 500 g/m2 of SAP. The first layer 41 according to the present embodiment is formed by mixing 280 g/m2 of pulp and 170 g/m2 of SAP.

The first layer 41 is formed with the central slit 45 and a pair of the side slits 46. The central slit 45 is formed in the central part in the widthwise direction W. The length of the central slit 45 in the front-back direction is longer than the length of the side slits 46 in the front-back direction. In the present embodiment, the central slit is 40 mm wide and each of the side slits 46 is 10 mm wide.

The second layer 42 is, for example, formed by mixing 100 to 500 g/m2 of pulp and 0 to 500 g/m2 of SAP. The second layer 42 according to the present embodiment is formed by mixing 260 g/m2 of pulp and 160 g/m2 of SAP.

The second layer 42 is formed in a shape of a glass hour. A central part in the longitudinal direction of the second layer 42 is a narrower part 42N of which a length in the widthwise direction is formed to be small An outside end of this narrower part 42N and an inside end of a side slit 46 are coincident with each other. According to such a structure, a difference in rigidity of the absorber 40 is formed at an end in the widthwise direction of the side slit 46, and the absorber can be stably bent with reference to the side slit 46.

Also, in the side slit 46, the topsheet 10 and the absorber back sheet 30 are adhered and secured to each other, thereby making it possible to bend the absorber without causing any deformation.

Further, as shown in FIG. 2, in the widthwise direction, an end of the auxiliary sheet 15 is positioned inside more significantly than the slide slit. Rigidity is different depending on a region in which the auxiliary sheet 15 is disposed and a region in which the auxiliary sheet 15 is not disposed (the region outside in the widthwise direction more significantly than the end in the widthwise direction of the auxiliary sheet 15). The difference in rigidity exerted by the presence or absence of the second sheet is provided, whereby curving can be easily made while a side curving unit which is composed of the side slit 46 is defined as a start point Additionally, as the central slit 45 is formed, a central part of the absorber 40 can easily bend convexly in the inward direction IN towards a wearer. The side slit 46 is formed at the outer side in the widthwise direction with respect to the central slit 45. The side slit 46 has a vertically long shape extending along the front-back direction. The pair of side slits 46 are formed on the absorber 40 along the front-back direction convexly in the outer direction OUT, that is, such that the absorber 40 bends convexly inverse to the central slit 45.

In the crotch region S3, an outer end 42W of the second layer 42 in the widthwise direction has overlap with an inner end 41W of the side slit 46 of the first layer, and is arranged along the front-back direction. The outer side in the widthwise direction of the second layer 42 beyond the outer end 42W is configured by the first layer 41 only, and the inner side beyond the outer end 42W is configured by the first layer 41 and the second layer 42, excluding the portion where the central slit 45 has been formed. Accordingly, the absorber 40 changes in rigidity and thickness at a boundary formed of the inner end 41W of the first layer 41 and the outer end 42W of the second layer 42. In the present embodiment, the absorber bends at a boundary formed of the outer end 42W of the second layer where the rigidity and other properties change.

(3) Changes in Shape of Absorber

Figure 6:
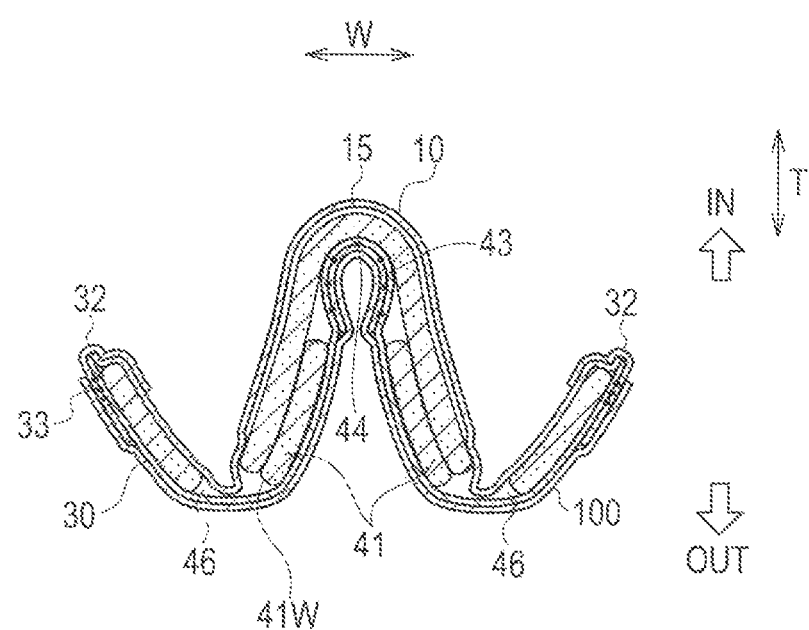
FIG. 6 is a sectional view taken along the line X1-X'1 schematically showing a deformed state of the disposable diaper according to the first embodiment.

FIG. 6 is a cross-sectional view (with reference to an X1-X'1 line of FIG. 1) that schematically illustrates the state when the disposable diaper 1 is worn. When the disposable diaper 1 is worn, the crotch region S3 of the absorber comes up against the crotch of the wearer. By the legs and the like of the wearer, force is applied on the absorber from the outer side in the widthwise direction toward the inner side in the widthwise direction. The absorber 40 bends at the side slits 46 as well as the central elastic member 44 and the central slit 45, and the cross-sectional shape of the disposable diaper 1 along the widthwise direction W is deformed in a wavelike manner. Thus, the crotch region S3 of the absorber 40 turns into a regularly folded-up condition.

The top surface of the absorber 40, which becomes convex in the inner direction IN due to the central elastic member 44, comes into contact with the crotch of the wearer. The portion where the convex portion, caused by the curving unit portion, is formed is configured by only the second layer 42, and is relatively thinner. On the other hand, the first layer 41 and the second layer 42 overlap between the convex portion caused by the curving unit and the convex portion caused by the side slit, this overlap being relatively thicker and more rigid. The convex portion formed of the curving unit can be supported by the portion having a high rigidity between the curving unit and the side slit, and the stability of the convex shape formed of the curving unit can be improved.

When the wearer closes both legs, with respect to the cross-sectional shape of the disposable diaper 1, the absorber is folded over at the curving unit and the side slits and is compactly arranged below the crotch in a state of close mutual contact.

At such a time, the curving unit formed of the central elastic member 44 and the central slit 45 is positioned so as to be in contact with the crotch of the wearer. On the other hand, the curving unit formed of the side slits 46, project towards the non-skin contact surface side and are at a position where it is difficult to contact with a wearer's excretion portion.

Because the absorber is in close contact at the crotch of the wearer, leakage of the body fluid can be prevented even in a case where urine is slowly excreted, which would run along the skin. In the folded state, a concavity extending in the front-back direction is formed at the curving unit of the portion of the absorber separated from the skin, and therefore the body fluid can be diffused outward in the front-back direction and side leakage can be prevented.

The absorber is folded up at the central slit 45 and the side slits 46 formed in the absorber so that the absorber 40 can bend more easily even when swollen by absorbing liquid compared with a case where the absorber 40 has a portion protruded by forming a thinner portion. The cross-sectional shape obtained when the disposable diaper 1 is worn and the absorber 40 is deformed is a tapered shape which narrows from the non-skin contact surface side to the skin contact surface side. Accordingly, the disposable diaper 1 can be easily fitted into the gap in the crotch of the wearer, and is less prone to cause discomfort.

Furthermore, the convex portion formed by the central elastic member 44 and the central slit 45 is configured only from the second layer 42, and is thinner than the portion configured by laminating the first layer 41 and the second layer 42. In other words, due to a thin and high structure, the convex portion formed by the central elastic member 44 and the central slit 45 can be inserted easily in the thin gap of the crotch, and easily adheres on to the excretion portion. Therefore, because the excretion portion and the absorber come in close contact, for example, the excreted urine can be absorbed rapidly. Furthermore, because the absorber is folded such that the thickness of the absorber is less in the portion close to the skin of the crotch of the wearer, and the thickness is more in the portion away from the skin, the absorber can be fitted without a feeling of discomfort.

When an opening unit and side slits are provided at both the first layer and the second layer, there may be positional deviation in case of laminating the first layer and the second layer. When the positional deviation occurs in, for example, the widthwise direction, the width of the pair of side slits arranged on the right and left is narrowed, regular deformation becomes impossible, and the absorber has a right-left imbalance, which may exert an adverse effect on absorption and on the feeling of comfort at the time of wearing. However, by providing an opening unit or side slits to at least one of the first layer and the second layer, the positional deviation of the side slits or the like can be prevented.

(4) Method of Manufacturing Absorbent Article

Figure 7:
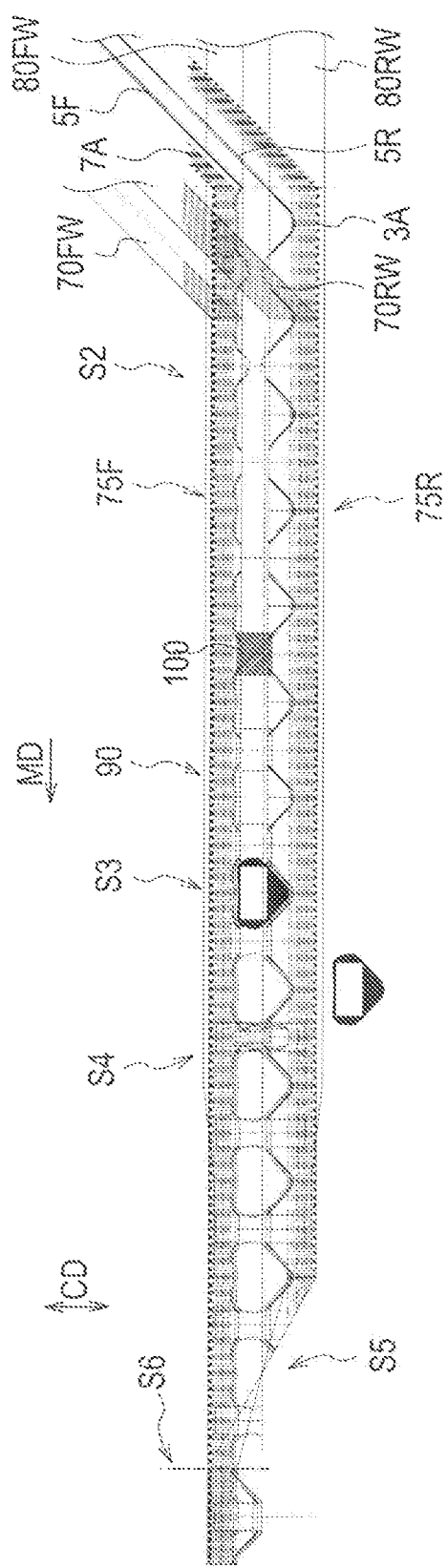
FIG. 7 is a view schematically showing the steps of manufacturing the absorbent article according to the first embodiment along a conveyance direction of a method of manufacturing the absorbent article.

One example of a method of manufacturing the absorbent article according to the present embodiment is explained. FIG. 7 is a view for explaining the method of manufacturing the absorbent article, and shows a part of the course in which the absorbent article is manufactured. In FIG. 7, a direction of conveying a constituent element in the manufacturing process is indicated as a conveyance direction MD, and a direction of crossing the conveyance direction is indicated as a crossing direction CD. In so far as the method of manufacturing the absorbent article is concerned, the absorbent article 1 is manufactured in a continuous state in the widthwise direction.

As far as the method that is not described in the present embodiment is concerned, the existing method can be used. Furthermore, the manufacturing method explained below is only an example, and the disposable diaper can also be manufactured by other manufacturing methods.

The method of manufacturing the absorbent article includes at least: an absorbent main body forming step S1; an exterior body forming step S2; the leg-holes forming step S3; a constituent element joining step S4; a folding step S5; a joining step S6; and a cutting step S7.

In the absorbent main body forming step S1, an absorbent main body 1A is formed. Specifically, for example, an absorption material is laminated to thereby mold an absorber 40; a leakage preventing unit is formed to be joined with a web constituting an absorber back sheet 30, and thereafter, an absorber 40 is disposed on the continuous web mentioned above; a web constituting a topsheet 10 is joined, and thereafter, the leakage preventing unit continuous bodies mentioned above at both sides are returned to the topsheet side, and a central elastic member 44 and an elastic member covering sheet are disposed. The step of disposing the central elastic member 44 and the elastic member covering sheet in the absorbent main body forming step S1 will be described later in detail.

In the exterior body forming step S2, an exterior body 1B is formed. The embodiment is configured so that: a foreside continuous body 75F in which an exterior sheet disposed at an abdominal side of a wearer is continuous and a backside continuous body 75R in which an exterior sheet disposed at a backside of the wearer is continuous are formed separately; the foreside continuous body 75F and the backside continuous body 75R are connected to each other via an exterior center sheet 100 so as to manufacture the exterior body 10B.

Specifically, between a foreside exterior sheet web 70FW which constitutes the foreside exterior topsheet 70F and a foreside exterior backsheet web FW80 which constitutes the foreside exterior back sheet 80F, a waistline elastic member 7A, a waist elastic member 3A, and a front leg-holes elastic member 5F are disposed to form a foreside continuous body 75F, and between a rearside exterior topsheet web 70RW which constitutes a rearside exterior topsheet 70R and a rearside exterior backsheet web 80RW which constitutes a rearside exterior backsheet 80RW, a waistline elastic member 7A, a waist elastic member 3A, and a back leg-holes elastic member 5R are disposed to form a backside continuous body 75R.

Next, an unrequired portion of the front leg-holes elastic member 5F and the back leg-holes elastic member 5R (a portion having overflowed to the outside from the foreside continuous body 75F and the backside continuous body 75R) is cut, and thereafter, the foreside continuous body 75F and the backside continuous body 75R are joined with each other by an exterior center sheet 100. In this manner, an exterior continuous body 90 in which the exterior body 1B of an individual product is continuous in a widthwise direction is formed.

In the leg-holes forming step S3, the exterior body 1B is cut along the front leg-holes elastic member 5F and the back leg-holes elastic member 5R. In this manner, an opening unit which is disposed at a leg hole of a wearer is formed.

In the constituent element joining step S4, the exterior body 1B and the absorbent main body 1A are joined with each other. Specifically, the absorbent main body 1A is disposed on the continuous body of the exterior body 1B at which the leg-holes opening unit is formed, and the absorbent main body 1A and the exterior body 1B are joined with each other via an adhesive agent.

In the folding step 55, the continuous body of the absorbent article in which the absorbent main body 1A and the exterior body 1B are joined with each other is folded over with reference to a fold including a center in a crossing direction and taken along a conveyance direction.

In the joining step S6, an end in the widthwise direction of the absorbent article that is folded over is joined. Specifically, a front waistline edge 4 and a rear waistline edge 6 are joined with each other, and a front waistline edge 4' and a rear waistline edge 6' are joined with each other.

In the cutting step S7, the continuous body of the absorbent article is cut in size of one product along the longitudinal direction (the crossing direction) of the absorbent article. In this manner, an absorbent article 1 is manufactured.

Figure 8:
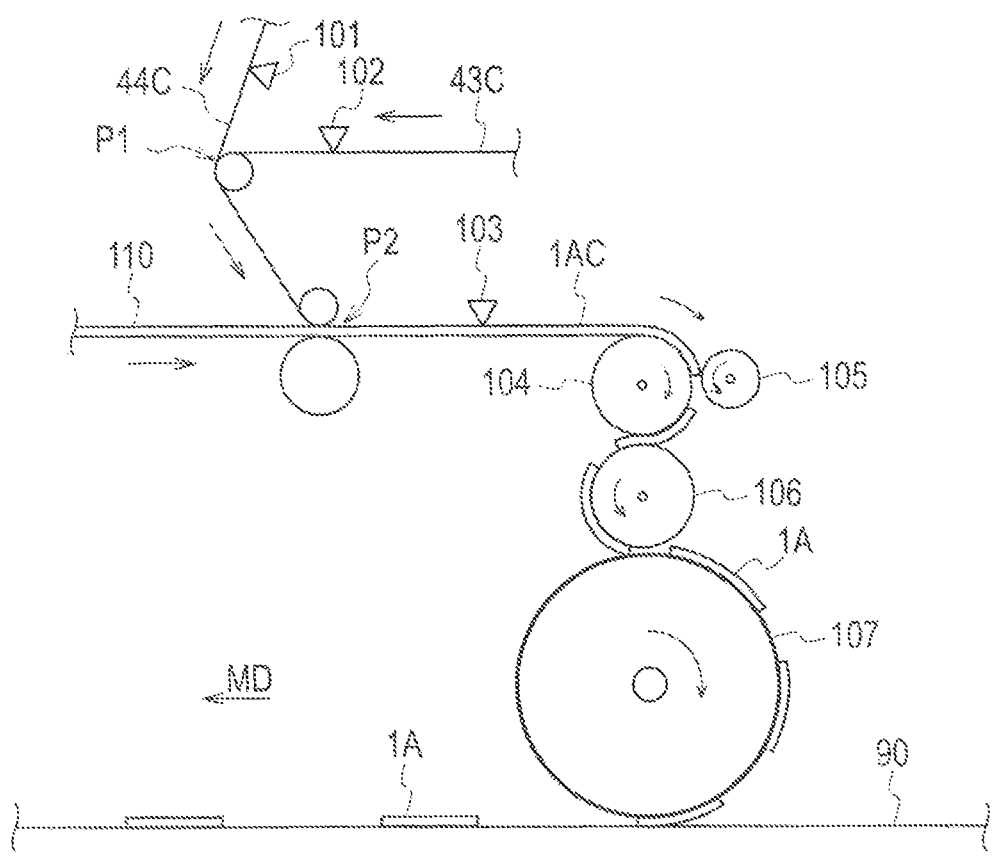
FIG. 8 is a view schematically showing the steps of manufacturing the absorbent article according to the first embodiment in a state in which the absorbent article is seen from a lateral side in a crossing direction of the method of manufacturing the absorbent article.

Next, referring to FIG. 8, a part of the steps of manufacturing the absorbent main body will be described in detail. FIG. 8 is a view schematically showing a part of the steps of manufacturing the absorbent main body in a state in which the absorbent article is seen from a lateral side in the crossing direction of the absorbent article.

First, a central elastic continuous body 44C in which an elastic member constituting a central elastic member 44 is continuous is conveyed in a state in which the continuous body is stretched in a conveyance direction MD. The central elastic continuous body 44C is conveyed in a state in which seven pieces are arranged in the crossing direction. Also, a covering continuous body 43C in which a web constituting the elastic member covering sheet 43 is continuous is conveyed toward the downstream side in the conveyance direction of the central elastic continuous body 44C, and at a joint point P1, the central elastic continuous body 44C and the covering continuous body 43C are joined with each other. At the downstream side in the conveyance direction more significantly than the joint point P1, the central elastic continuous body 44C and the covering continuous body 43C are conveyed so as to be joined with each other.

In addition, a main body continuous body 11C in which a main body unit constituting an absorbent main body is continuous is conveyed toward the downstream side in the conveyance direction of the central elastic continuous body 44C and the covering continuous body 43C, and at a joint point P2, the main body continuous body 11C, the central elastic continuous body 44C, and the covering continuous body 43C are joined with each other. It is to be noted that, from among the constituent elements constituting the absorbent main body, the main body unit is composed of constituent elements other than the central elastic member and the elastic member covering sheet. In so far as the main body continuous body 11C is concerned, sheet materials for the topsheet, the leakage preventing sheet, and the absorber back sheet or the like are continuous, and therebetween a discontinuous bodies such as the absorber and the second sheet are disposed. The main body continuous body 11C is conveyed in a state in which a face on the absorber back sheet side is oriented upward (to the side at which the central elastic member and the elastic member covering sheet are joined with each other). In so far as the downstream side more significantly than the joint point P2 is concerned, at the downstream side in the conveyance direction more significantly than the joint point P2, an absorbent main body continuous body 1AC is conveyed in a state in which the main body continuous body 11C, the central elastic continuous body 44C, and the covering continuous body 43C are joined with each other, that is, in a state in which the absorbent main body is continuous.

At the upstream side in the conveyance direction more significantly than the joint point P1 at which the central elastic continuous body 44C and the covering continuous body 43C are joined with each other, an adhesive agent such as a hot melt type adhesive agent is discontinuously applied to the central elastic continuous body 44C by a first adhesive agent applying device 101. In the embodiment, by the first adhesive agent applying device 101, the adhesive agent is directly applied to the central elastic continuous body by basis weight of 0.03 g/m2 in accordance with a V-slot approach.

Figure 9:
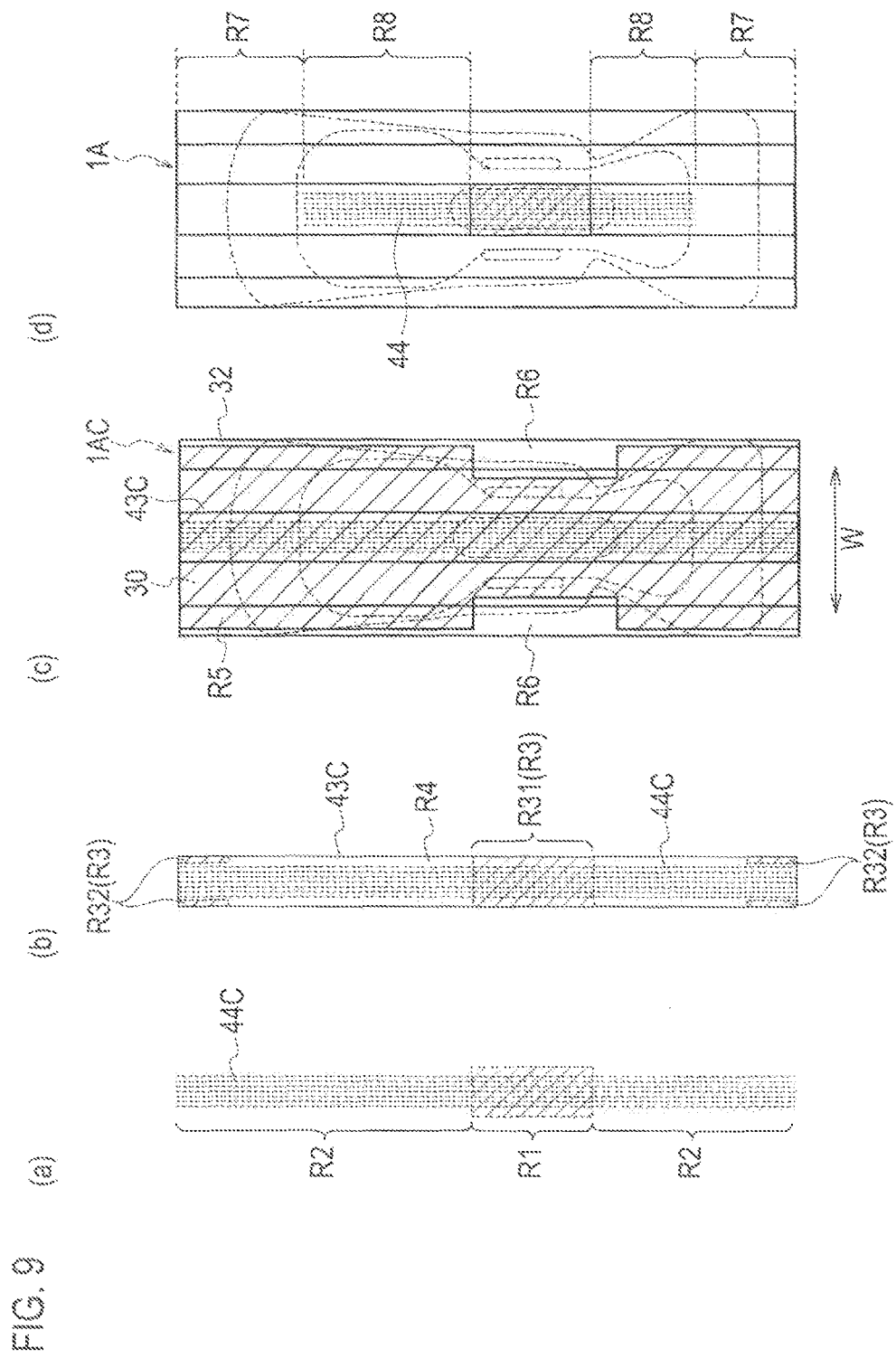
FIGS. 9A-9D are views for explaining the step of forming an absorbent main body.

At the central elastic continuous body 44C, a first application region R1 in which the adhesive agent is applied by the first adhesive agent applying device and a first non-application region R2 in which the adhesive agent is not applied are alternately formed in the conveyance direction (the first step). FIG. 9 is a view for explaining the step of forming the absorbent main body, and FIG. 9 (a) shows a state in which the adhesive agent is applied to the central elastic continuous body by the first adhesive agent applying device. For the sake of convenience of explanation, the first application region R1 is indicated by the shaded line.

The first application region R1 corresponds to a region in which the central elastic member 44 is disposed in a stretched state, in a product state (subsequent to the step of cutting the central elastic continuous body 44C, which will be described later). The first non-application region R2 corresponds to a region in which the central elastic member 44 in a non-stretched state is disposed in a product state (subsequent to the step of cutting the central elastic continuous body 44C, which will be described later) and a region in which, although the central elastic continuous body 44C is disposed prior to the step of cutting the central elastic continuous body 44C, the central elastic member 44 is not disposed in the product state.

A length in the longitudinal direction of the first application region R1 is a length at which a central elastic member is to be disposed in a stretched state, and the length in the embodiment is 120 mm The length in the longitudinal direction of the first application region R1 is obtained as a length at which the elastic member is deformed to a wearer's side in a protrusive manner, and is defined so as to correspond to a site to be worn at a site which is positioned at the narrowest part of a crotch of a wearer.

For example, if the first application region R1 is stretched to the foreside too mush, when the absorber 40 is deformed in a protrusive manner (in the state shown in FIG. 6), the central elastic member 44 occasionally acts so as to impart a sense of compression to a lower abdominal part. On the other hand, if the first application region R1 is stretched to the backside too much, a central portion of the absorber rises at the buttocks side, whereby a wearer's body is pressed. Therefore, a space which is capable of absorbing the bodily waste flowing to the hip side is reduced, and there is an apprehension that the leakage exerted by the bodily waste flowing to the outside of the widthwise direction occurs.

Also, at the upstream side in the conveyance direction more significantly than the joint point P1 at which the central elastic continuous body 44C and the covering continuous body 43C are joined with each other, an adhesive agent such as a hot melt type adhesive agent is applied to a face of the central elastic continuous body side of the covering continuous body 43C by a second adhesive applying device 102. In the embodiment, by the second adhesive agent applying device 102, the adhesive agent is applied to the covering continuous body 43C by basis weight of 7 g/m2 in accordance with a contact application process based upon a Slot Coater approach On the face of the central elastic continuous body side of the covering continuous body 43C, there are formed: a second application region R3 in which the adhesive agent is applied by the second adhesive agent applying device; and a second non-application region R4 in which the adhesive agent is not applied. The second application region R3 has: a central second application region R31 which is formed at a position corresponding to the first application region R1; and a terminal second application region R32 which is formed at a respective one of a front end and a back end of the elastic member covering sheet 43. FIG. 9 (b) shows a state in which the adhesive agent is applied to the covering continuous body 43C by the second adhesive agent applying device 102. For the sake of convenience of explanation, the central second application region R31 and the terminal second application region R32 are indicated by the shaded line.

The central second application region R31 and the first application region R1 are coincident with each other in length of the longitudinal direction. By the central second application region R31, the elastic member covering sheet 43 and the absorber back sheet 30 can be adhesively bonded with each other, and the central elastic member 44 can be secured in a stretched state between the elastic member covering sheet 43 and the absorber back sheet 30.

It is to be noted that, in the embodiment, although he central second application region R31 is provided, the central second application region R31 may not be provided. In a case where the central second application region R31 is not provided, for example, by the first application region R1, the central elastic member 44 can be secured in a stretched state between the elastic member covering sheet 43 and the absorber back sheet 30, and by the terminal second application region R32, the elastic member covering sheet 43 and the absorber back sheet 30 can be adhesively bonded with each other.

The terminal second application region R32 is provided at a respective one of the four corners of the elastic member covering sheet 43 in a planar view shown in FIG. 9 (b). A length in the widthwise direction of each of the terminal second application regions R32 is 3 mm, and a length in the longitudinal direction is 40 mm. It is to be noted that, when the adhesive agent is applied by the second adhesive agent applying device 102, the adhesive agent is applied to the covering continuous body 43C in a state in which the elastic member covering sheet 43 is continuous. Therefore, the second adhesive agent applying device continuously forms two terminal second application regions R32, and applies the adhesive agent in length for 40 mm×two products.

Since the terminal second application regions R32 are provided at the four corners of the elastic member covering sheet 43, the corners of the elastic member covering sheet 43 can be secured to the absorber back sheet 30, and opening of the sheet is prevented.

It is desirable that the terminal second application region R32 be provided at a position which does not overlap with the central elastic member 44. The terminal second application region R32 and the central elastic member 44 are provided so as not to overlap with each other, thereby making it possible to prevent the appearance from being degraded due to turning up of the elastic member covering sheet 43 at the time of cutting or due to the sheet being transferred while in folded state.

Also, since the terminal second application region R32 is discontinuously formed, soft finishing is possible in comparison with a continuously formed structure, and cost reduction is also possible.

In addition, since the elastic member covering sheet 43 is provided at the non-skin contact surface side of the absorber back sheet 30 separately from the sheets that envelopes an absorber core (the absorber back sheet 30 and the leakage preventing side sheet 32), for example, even in a case where the elastic member covering sheet 43 is spaced from the absorber back sheet 30, the leakage of the bodily liquid that is absorbed by the absorber can be prevented.

Incidentally, it is sufficient if the elastic member covering sheet 43 be a minimum width dimension to such an extent as to be able to cover the central elastic member. Also, it is desirable that the elastic member covering sheet 43 be a sheet made of a nonwoven cloth sheet is comparatively low in basis weight.

In addition, at the downstream side in the conveyance direction more significantly than the joint point P2, an adhesive agent such as a hot melt type adhesive agent is applied to an absorbent main body continuous body 1AC by a third adhesive agent applying device 103. The third adhesive agent applying device 103 applies the adhesive agent by a CS (Control Seam) approach, a non-contact type method such as a spiral approach, or a contact type approach such as a Slot Coater. In the embodiment, in the CS approach, the adhesive agent was applied in amount of 6 g/m2.

By the third adhesive agent applying device 103, the adhesive agent is applied to a face of the absorber back sheet of the absorbent main body continuous body (the face to be joined with an exterior continuous body 90). The face of the absorber back sheet side of the absorbent main body continuous body 1AC is composed of: a absorber back sheet continuous body; and the covering continuous body 43C which is disposed on the absorber back sheet continuous body via the central elastic continuous body 44C.

On the face of the absorber back sheet side of the absorbent main body continuous body 1AC, a third application region R5 in which the adhesive agent is applied by the third adhesive agent applying device 103 and a third non-application region R6 in which the adhesive agent is not applied are formed. FIG. 9 (*c*) shows a state in which the adhesive agent is applied by the third adhesive agent applying device. For the sake of convenience of explanation, the third application region R5 is indicated by the shaded line.

The third application region R5 includes all of the region in which the covering continuous body 43C is disposed, and the application region is disposed except a part of both ends in the widthwise direction of the absorber back sheet. The third non-application region R6 is provided on the outside of the widthwise direction more significantly than a region in which the length in the widthwise direction of the first layer 41 of the absorber 40 is the smallest By the adhesive agent of the third application region R5, the absorbent main body 1A and the exterior body 1B can be adhesively bonded with each other. Also, the adhesive agent that is applied to the covering continuous body 43C by the third adhesive agent applying device 103 permeates to the inside of the covering continuous body 43C (a gap between the fibers of the nonwoven cloth constituting the covering continuous body), and permeates up to the face of the absorber back sheet side of the covering continuous body 43C (the second step). In order to permeate the adhesive agent up to the face of the absorber back sheet side of the covering continuous body 43C, for example, the adhesive agent can be applied in basis weight of 5 g/m2 to 30 g/m2. By the adhesive agent having permeated the covering continuous body 43C, the central elastic member 44 is temporarily secured, and it is possible to restrain movement of the central elastic member 44 in an unintended direction . A specific description will be given later. In addition, the basis weight of the adhesive agent is an application amount of the adhesive agent per unit area, and the application amount thereof can be measured in accordance with JIS K6833-1, for example.

Next, the absorbent main body continuous body 1AC to which the adhesive agent is thus applied is supplied to a first rotor 104 and then is conveyed along an outer circumferential face of the first rotor 104. In the course of conveying the absorbent main body continuous body 1AC along the outer circumferential face of the first rotor 104, the continuous body is cut in individual product length by a cutting rotor 105 which is disposed in opposite to the first rotor 104. In this manner, an absorbent main body 1A is formed. The cutting rotor 105 cuts an front end and a back end of the absorbent main body along a widthwise direction.

These ends are cut by the cutting rotor, whereby the continuous bodies such as the covering continuous body 43C, an absorption back face continuous body, and the central elastic continuous body 44C are cut (the third step). The central elastic continuous body is cut, whereby the product length of the individual central elastic member 44 is obtained, and the stretched state is released. FIG. 9 (*d*) is a view showing an absorbent main body in a state subsequent to cutting of the absorbent main body continuous body 1AC.

At this time, the central elastic member 44 that is disposed in the first application region R1 prior to cutting is secured between the absorber back sheet 30 and the elastic member covering sheet 43 subsequent to cutting as well, by the adhesive agent that is applied by the first adhesive agent applying device 101, the adhesive agent that is applied by the second adhesive agent applying device 102, and the adhesive agent that is applied by the third adhesive agent applying device 103, and that permeates the covering continuous body 43C. The central elastic member 44 that is disposed in the first application region R1 is secured in the stretched state in the longitudinal direction in the same manner as that in the state prior to cutting. A region in which the central elastic member 44 in the stretched state is disposed is obtained as a stretched region which is shrunk in the longitudinal direction by the central elastic member 44. Therefore, the first application region R1 is obtained as a stretched region in which the central elastic member 44 is disposed in the stretched state.

On the other hand, the central elastic member 44 that is disposed in the first non-application region R2 prior to cutting shrinks in the longitudinal direction subsequent to cutting, and is retained in a non-stretched state between the absorber back sheet 30 and the elastic member covering sheet 43. The central elastic member 44 is shrunk by cutting, whereby a central elastic member non-disposition region R7 in which the central elastic member is not disposed is formed at a respective one of a front end and a back end of the first non-application region R2.

A central elastic member non-stretched region R8 in which the central elastic member 44 is disposed in a non-stretched state is provided between the central elastic member non-disposition region R7 and the first application region R1. The central elastic member 44 of the central elastic member non-stretched region R8 is applied by the third adhesive agent applying device, and is secured between the absorber back sheet 30 and the elastic member covering sheet 43 by the adhesive agent that permeates the covering continuous body 43C. The central elastic member non-disposition region R7 and the central elastic member non-stretched region R8 each are obtained as a non-stretched region which is not shrunk by the central elastic member 44.

For example, in a case where no adhesive agent is applied to the central elastic member 44 that is disposed in the central elastic non-stretched region R8, since the central elastic member 44 in the non-stretched state arbitrarily moves, there may be a case in which the central elastic member 44 in the non-stretched state is displaced to the outside of the elastic member covering sheet and then turns to the left or right, a plurality of central elastic members 44 overlap or cross each other irregularly. Thus, if the central elastic member 44 in the non-stretched state, which is cut, and a stretched state of which is released, arbitrarily moves, there is an apprehension that a feeling of discomfort in appearance or an impairment of a feeling of comfort at the time of wearing occurs. However, the central elastic member 44 in the stretched state is retained by the adhesive agent having permeated the elastic member covering sheet 43, whereby a position of the central elastic member 44 can be secured in a given region (in the first non-application region R2).

Further, the central elastic member 44 in the non-stretched state is retained by the adhesive agent having permeated the elastic member covering sheet 43, whereby, even in a case where a product is moved prior to wearing, it is possible to restrain displacement of the central elastic member 44 in the non-stretched state in the widthwise direction, bending of the central elastic member 44 in the non-stretched state, or overlapping of the central elastic members 44 in the non-stretched state. Moreover, it is possible to restrain coming-off and movement of the central elastic member 44 in the non-stretched state due to a movement exerted while being worn by a wearer as well. Therefore, at the time of wearing as well, it is possible to retain the position or the shape of the central elastic member in the non-stretched state and restrain an abnormality such as a feeling of discomfort in appearance or an impairment of a feeling of comfort at the time of wearing. Further, since the adhesive agent to retain the central elastic member 44 in the non-stretched state is permeation of a part of the adhesive agent for adhering the exterior body 1B and the absorbent main body 1A to each other, there is no need for an additional step or facility of applying an adhesive agent for retaining the central elastic member 44 in the non-stretched state, and the manufacturing steps can be simplified.

In addition, the third application region R5 is provided across the first application region R1 and the first non-application region R2, and overhangs a shrinkage region which is shrunk by the central elastic member 44 and a non-shrinkage region which is not shrunk by the central elastic member 44. Therefore, when the adhesive agent is applied by the third adhesive agent applying device 103, there is no need to control the application region so as to be aligned to the boundary between the first application region R1 and the first non-application region R2, and the adhesive agent can be applied by simple control.

Thus, in the first application region R1, there are disposed: the adhesive agent that is applied by the first adhesive agent applying device 101; the adhesive agent that is applied by the second adhesive agent applying device 102; and the adhesive agent that is applied by the third adhesive agent applying device 103, and permeates the covering continuous body 43C. On the other hand, in the first non-application region R2, there is disposed only the adhesive agent that is applied by the third adhesive agent applying device 103, and that permeates the covering continuous body 43C. Therefore, the basis weight of the adhesive agent in the first application region R1 is higher than the basis weight of the adhesive agent in the first non-application region R2. According to such a structure, the central elastic member 44 in the stretched state can be strongly secured by the adhesive agent in the first application region, and the central elastic member 44 in the stretched state can be comparatively weakly secured by the adhesive agent in the first non-application region R2.

The central elastic member 44 in the stretched state is strongly secured by the adhesive agent in the first application region, whereby the length or the position in the stretched region can be stabilized. For example, in a case where a stretch region is formed at a position which overlaps with the absorber (such as a slit), if a displacement in the stretched region occurs, there is an apprehension that a redundant wrinkle occurs with the absorber. However, by restraining the displacement in the stretched region, it is possible to restrain degradation in fitting property at the time of wearing or degradation in absorption performance.

Also, the absorbent main body 1A and the exterior body 1B are adhesively bonded with each other by the adhesive agent that is applied to the third application region R5. The third application region R5 is not an entire face of the exterior body 1B side of the absorbent main body 1A. At a part of the absorbent main body (in a region in which no absorber is disposed), the third non-application region R6 is provided. Since the absorbent main body 1A and the exterior body 1B are partially adhesively bonded with each other by the adhesive agent, the ventilation property of the exterior body can be ensured while an occurrence of a wrinkle or a folding of the absorber is prevented. In particular, since the third non-application region R6 is provided in the crotch region S3, the exterior body 1B does not inhibits deformation of the absorber exerted by the side slits 46, and in addition, even in a case where the crotch width of the absorber 40 is narrowed due to a W-shaped deformation of the absorber, the skin can be covered with the exterior body 1B, and an occurrence of a leakage can be restrained.

Also, the third application region R5 is provided on the outside of the widthwise direction of the elastic member covering sheet 43, and is also provided along the outside of the widthwise direction of a central elastic member non-stretch region R8. Therefore, even if the central elastic member 44 that is weakly adhesively bonded comes off, there does not occur a movement in a widthwise direction in such a manner as to overflow from the elastic member covering sheet 43, and the appearance can be ensured.

In addition, after the absorbent main body continuous body 1AC has been cut by the cutting rotor 105, the absorbent main body 1A is led from a first rotor 104 to a second rotor 106. After the absorbent main body 1A has been conveyed along an outer circumferential face of the second rotor 106, the absorbent main body is led to a direction change rotor 107. The direction change rotor 107 is provided with a plurality of adsorption unit which are not shown; rotates about a shaft along a radial direction of the rotor while retaining the absorbent main body 1A at the adsorption unit; and changes a direction of the absorbent main body 1A.

The absorbent main body 1A arrives at the direction change rotor 107 in a continuous state in a longitudinal direction; is rotated by 90 degrees by the direction change rotor 107; and is conveyed while being disposed so as to be spaced in a widthwise direction. In addition, the absorbent main body 1B is disposed on the exterior continuous body 90 in which the exterior body 1B is continuous. The subsequent steps can be achieved by the method of manufacturing the absorbent article as mentioned above.

Also, since the central elastic member 44 is disposed in an outer direction OUT more significantly than the leakage preventing sheets (the absorber back sheet 30 and the leakage preventing side sheets 32), even in a case where the central elastic member 44 is cut after being disposed in the continuous state, as in the embodiment, there is no need to provide a gap or the like for cutback) at a portion which is surrounded by the leakage preventing sheet, and it is possible to prevent a leakage of bodily liquid while maintaining the sealing property of the leakage preventing sheet that envelopes the absorber.

It is to be noted that the present invention can be preferably employed in a case in which a length of the central elastic member 44 that is disposed in the stretched state subsequent to cutting (the length of the first application region in the embodiment) is comparatively small with respect to a length of the central elastic member 44 that is disposed in the stretched state prior to cutting (the length in the longitudinal direction of the absorbent main body 1A in the embodiment).

This is because, in the case in which the length of the central elastic member 44 that is disposed in the stretched state subsequent to cutting is comparatively small with respect to the length of the central elastic member 44 that is disposed in the stretched state prior to cutting, a ratio in length of an elastic member to be cut back increases, and the appearance is greatly affected. Further, in a case where an expansion rate of the elastic member is small, it is effective since the length of the elastic member to be cut back increases.

In the embodiment, a ratio of the length of the central elastic member 44 that is disposed in the stretched state subsequent to cutting, with respect to the length of the central elastic member 44 that is disposed in the stretched state prior to cutting, is about 0.19; the expansion rate is 2.0 times (100% expansion), and a total length (foreside+backside) to be cut back is about 260 mm. In a case where a rate of the stretch region is small in comparison with a rate of the non-stretch region, in particular, in a case where the expansion rate of the elastic member is set to be low, a length of a free elastic member which is not adhesively secured increases; and however, in that case as well, the appearance can be appropriately maintained.

Further, it is preferable that the ratio of the length of the central elastic member 44 that is disposed in the stretched state subsequent to cutting, with respect to the length of the central elastic member 44 that is disposed in the stretched state prior to cutting, be ½ or less, and an advantageous effect is attained in the case where the ratio is ⅓ or less. The advantageous effect is attained when the expansion ratio is comparatively low. For example, if the expansion ratio is set to be high, the thickness of the elastic member decreases, and the adhesive area decreases, and thus, it is difficult to carry out shrinking while maintaining a stretching trajectory of the elastic member. Further, if the expansion rate is set to be high, a return stress of the elastic member also increases. Therefore, in the case where the expansion rate is set to be high, there is a need to increase an application amount of the adhesive agent and increase a permeation amount. However, if the application amount of the adhesive agent is excessive, there is an apprehension that the sheet hardens or the costs increase. From such a point of view, it is desirable that the expansion rate of the central elastic member 44 be 1.2 times to 3.0 times, and in particular, it is preferable that the rate be 2.5 times or less (150% expansion).

Also, in so far as the method of manufacturing the absorbent article according to the embodiment is concerned, the elastic continuous body 44C is configured so as to join with the main body continuous body 11C immediately before the absorbent main body 1A is adhered to the exterior body 1B. For example, if a joint point to join the central elastic continuous body 44C with the main body continuous body 11C is set at the upstream side in the conveyance direction, when the main body continuous body 11C is conveyed, the main body continuous body 11C is shrunk by the central elastic continuous body 44C, and there is an apprehension that the main body continuous body 11C partially turns up. However, the joint point at which the central elastic continuous body 44C is joined with the main body continuous body 11C is provided immediately before adhering the absorbent main body 1A to the exterior body 1B, thereby making it possible to prevent an unintended shrinkage or turning up of the main body continuous body 11C.

(5) Modification Example

Next, a disposable diaper according to each of Modification Examples will be described referring to FIG. 10. It is to be noted that, in the following embodiment, same constituent elements in the foregoing embodiment are designated by same reference numerals, and a duplicate description thereof is omitted.

Figure 10:
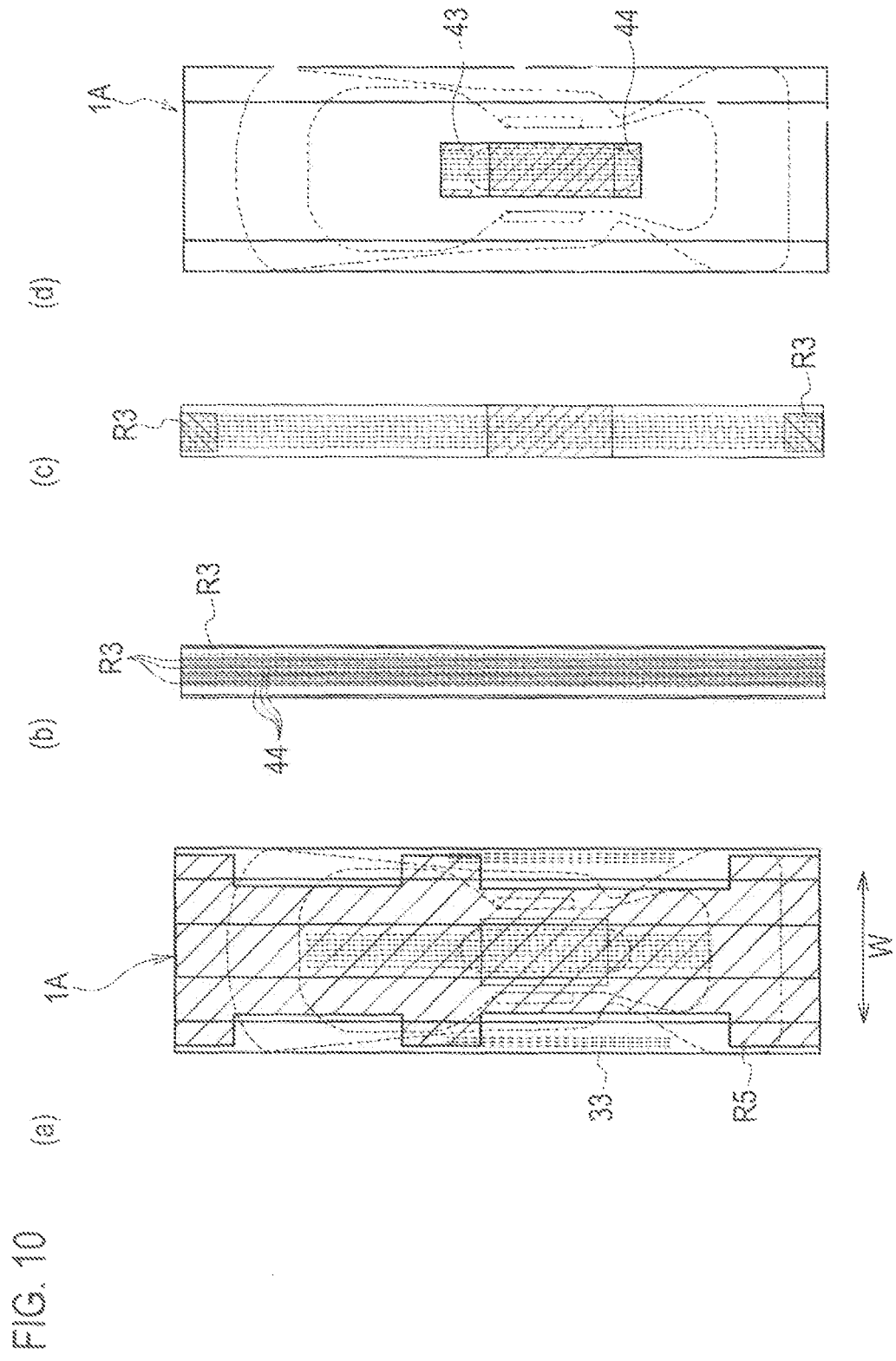
FIGS. 10A-10D are views for explaining a method of manufacturing the absorbent article, according to a modification example.

FIG. 10 (a) is a view showing a third application region R5 which is provided at an absorbent main body according Modification Example 1. The third application region R5 of Modification Example 1 is smaller in area than the third application region R5 of the embodiment. An area in which an adhesive agent is to be applied is small, and the product can be softly finished while the advantageous effect of the present invention is attained.

Although the third application region R5 of the embodiment is provided so as to cover the entire face of the elastic member covering sheet 43, the third application region R5 of a respective one of Modification Examples is not provided at a stretching securing unit (the first application region R1) of the central elastic member 44, and is discontinuously provided. Also, in so far as the third application region R5 of each of Modification Examples is concerned, an application length of a portion to be widely applied is reduced more remarkably than that of the third application region R5 of the embodiment, and is smaller in foreside and backside.

In addition, at a hip side portion as a start point for occur with respect to an erection which is exerted by shrinkage of the leakage preventing elastic member 33, the third application region R5 is discontinuously disposed. For example, if an erection height is too high at the hip side, an erected portion falls down to the inside and then obstructs a topsheet as an absorption face, and there is an apprehension that the absorption performance lowers. However, by restraining the erection height at the hip side, it is possible to restrain lowering of the absorption performance due to the fact that the erection height is too high at the hip side.

FIG. 10 (b) shows a second application region R3 according to Modification Example 2. The second application region R3 of Modification Example 2 is provided between each side in a widthwise direction of an elastic member covering sheet 43 and a central elastic member 44 which is adjacent thereto. The second application region R3 is thus disposed to thereby decrease a width of which a respective one of the central elastic members 44 can move to the left and right. Further, it is possible to prevent crossing of at least a cutback unit of the adjacent central elastic members 44.

FIG. 10 (c) shows a second application region R3 according to Modification Example 3. The second application region R3 of Modification Example 3 is provided at an end in a longitudinal direction of an elastic member covering sheet 43. According to such a structure, it is possible to adhere to an absorber back sheet 30 all over the end in the longitudinal direction of the elastic member covering sheet 43, and it is also possible to reduce opening of the elastic member covering sheet 43.

FIG. 10 (d) shows an elastic member covering sheet 43 according to Modification Example 4. The elastic member covering sheet 43 according to Modification Example 4 is smaller than a length in a longitudinal direction of an absorbent main body 1A, and is disposed at only a portion at which an elastic member is to be stretched and secured. It is possible to reduce a length in a longitudinal direction of the elastic member covering sheet and a length of a central elastic member 44, and it is possible to reduce the costs.

A length in a widthwise direction of the elastic member covering sheet 43 of Modification Example 4 is about twice of the elastic member covering sheet 43 of the embodiment, and this sheet is folded into two sections in the widthwise direction. In so far as the step of disposing the elastic member covering sheet 43 and the central elastic member 44 according to Modification Example 4 is concerned, for example, an adhesive agent is applied to a region in which central elastic members of a central elastic continuous body are secured in a stretched state, and an adhesive agent is applied to a region in which central elastic members of a covering continuous body are secured in a stretched state, and thereafter, the central elastic continuous body is adhered between the covering continuous body and then is folded into two sections. Afterwards, an adhesive agent is applied from the outside of the covering continuous body. At this time, the adhesive agent is applied so as to overhang on a region in which the central elastic members are secured in the stretched state and a region in which the central elastic members are not secured in the stretched state. Next, the covering continuous body and the central elastic continuous body are cut in individual product length. The adhesive agent that is applied from the outside of the covering continuous body permeates the inside of the covering continuous body, whereby it is possible to retain the cut back central elastic members in the region in which the central elastic members are not secured in the stretched state.

(6) Other Embodiments

As described above, although the content of the present invention was disclosed through the embodiments of the present invention, the descriptions and drawings that form a part of this disclosure are not to be considered as limitation to the present invention. From this disclosure, a variety of alternate embodiments, examples, and applicable techniques will become apparent to one skilled in the art.

For example, while, in the foregoing embodiment, a disposable diaper of a pants-type was described by way of example, the present invention is not limited thereto, and may be applied to an open-type disposable diaper, an incontinence pad, and a sanitary napkin or the like.

While, in the foregoing embodiment, an adhesive agent is applied to a face of the absorber back sheet side of the absorbent main body 1A by the third adhesive agent applying device, the present invention is not limited to this structure. For example, an adhesive agent may be applied to a face of the absorbent main body side of the exterior body 1B. It may be that the adhesive agent that is applied to the face of the absorbent main body side of the exterior body 1B permeates the inside of the elastic member covering sheet 43 so as to be exposed to the face on the absorber back sheet 30 side of the elastic member covering sheet 43.

In addition, while, in the embodiment, a third application region is disposed so as to include a stretched region and a non-stretched region, the present invention is not limited to this structure. It is sufficient if the third application region include at least the non-stretched region.

While, in the foregoing embodiment, an elastic member covering sheet to be permeated by an adhesive agent is composed of a nonwoven cloth, for example, the sheet may be composed of an opening film in which a plurality of very small holes are formed.

While, in the foregoing embodiment, a structure is employed so that, after a continuous absorbent main body in a longitudinal direction has been cut, the absorbent main body after cut is directionally changed at 90 degrees and then is adhered to the exterior body 1B, the present invention is not limited to this structure.

In aforementioned embodiments, the absorber 40 has a bi-layered structure of the first layer 41 and the second layer 42, but the absorber 40 of the worn article according to further embodiments may be configured from a single layer or may be configured from three or more layers As described above, needless to say, the present invention includes various embodiments and the like not described here. Accordingly, the scope of the present invention is defined only by the appended claims in view of the above description.

The entire contents of Japanese Patent Application No. 2012-137206 (filed on Jun. 18, 2012) are incorporated in the present specification by reference.

INDUSTRIAL APPLICABILITY

It is possible to provide an absorbent article and a method of manufacturing the absorbent article that are capable of alternatively disposing an elastic member in a stretched state and an elastic member in a non-stretched state, and that is capable of restraining a feeling of discomfort in appearance or an impairment of a feeling of comfort at the time of wearing while restraining a position or a shape of the elastic member in the non-stretched state

The invention claimed is:
1. An absorbent article comprising:
  a longitudinal direction which extends between a body foreside and a body rearside of a wearer;
  a widthwise direction perpendicular to the longitudinal direction;
  an inner direction which is oriented to the wearer;
  an outer direction which is oriented to an opposite to the inner direction;
  a crotch region which is applied for a crotch of the wearer;
  a front waistline region which is disposed at a front side of the crotch region;
  a rear waistline region which is disposed at a rear side of the crotch region;
  an absorber which is disposed at least in the crotch region;
  an elastic member which is disposed in an extended state in the longitudinal direction in the outer direction than the absorber; and
  a sheet member which is disposed on a face of the outer direction of the elastic member, and which abuts against the elastic member,
  wherein the sheet member is disposed so as to cover: a stretch region in which the elastic member is disposed in a stretched state in the longitudinal direction; and a non-stretch region in which the elastic member is disposed in a non-stretched state,
  wherein a first adhesive agent is disposed to an inner surface or an outer surface of the elastic member in the stretch region,
  a second adhesive agent is disposed between the sheet member and the elastic member in the stretched state in the stretch region,
  the sheet member is joined with the elastic member,
  wherein a third adhesive agent is disposed to an outer surface of the sheet member at least in the non-stretch region, and wherein a fourth adhesive agent permeated by the third adhesive agent that is applied to an outer surface of the sheet member is disposed on an inner surface of the sheet member, basis weight of the fourth adhesive agent that is disposed on an inner surface of the sheet member is smaller than basis weight of the first adhesive agent that is disposed to an inner surface or an outer surface of the elastic member in the stretch region.

2. The absorbent article according to claim 1, wherein the sheet member consists of a nonwoven cloth.

3. The absorbent article according to claim 1, wherein a slit extending in the longitudinal direction is formed at the absorber, and wherein the elastic member is disposed so as to overlap with the slit.

4. The absorbent article according to claim 1, wherein a liquid-impermeable leakage preventing sheet is provided between the absorber and the elastic member.

5. The absorbent article according to claim 1, wherein an absorbent main body having the absorber, a liquid-permeable topsheet which is disposed in the inner direction than the absorber, and a liquid-impermeable leakage preventing sheet which is disposed in the outer direction than the absorber; and an exterior body which is disposed in an outer direction than the absorbent main body, and which is disposed at a crotch and a waistline of the wearer, the stretch region and the non-stretch region are alternately disposed in a longitudinal direction, the non-stretch region is disposed at each end in the longitudinal direction of the absorbent main body, and the stretch region is disposed between the non-stretch regions.

6. The absorbent article according to claim 1, comprising:

an absorbent main body having the absorber, a liquid-permeable topsheet which is disposed in the inner direction than the absorber, and a liquid-impermeable leakage preventing sheet which is disposed in the outer direction than the absorber; and an exterior body which is disposed in an outer direction than the absorbent main body, and which is disposed at a crotch and a waistline of the wearer, wherein the leakage preventing sheet covers at least the outer surface of the absorber, and wherein the elastic member and the sheet member are disposed on an outer surface of the leakage preventing sheet.

* * * * *